US009681971B2

(12) United States Patent
Wang

(10) Patent No.: US 9,681,971 B2
(45) Date of Patent: *Jun. 20, 2017

(54) METHODS FOR CRIMPING A POLYMERIC SCAFFOLD TO A DELIVERY BALLOON AND ACHIEVING STABLE MECHANICAL PROPERTIES IN THE SCAFFOLD AFTER CRIMPING

(71) Applicant: Abbott Cardiovascular Systems Inc., Santa Clara, CA (US)

(72) Inventor: Yunbing Wang, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/867,919

(22) Filed: Sep. 28, 2015

(65) Prior Publication Data
US 2016/0030216 A1    Feb. 4, 2016

Related U.S. Application Data

(60) Division of application No. 14/263,961, filed on Apr. 28, 2014, now Pat. No. 9,155,870, which is a
(Continued)

(51) Int. Cl.
*B23P 11/02* (2006.01)
*A61F 2/06* (2013.01)
(Continued)

(52) U.S. Cl.
CPC .............. *A61F 2/958* (2013.01); *A61L 31/06* (2013.01); *A61L 31/16* (2013.01); *A61M 25/1034* (2013.01); *B23P 11/025* (2013.01); *B29D 23/00* (2013.01); *A61F 2002/9522* (2013.01); *A61F 2240/001* (2013.01); *B29K 2067/043* (2013.01); *B29K 2067/046* (2013.01);
(Continued)

(58) Field of Classification Search
CPC .. A61F 2/962; A61F 2/958; A61F 2/91; B23P 11/025; Y10T 29/499929; Y10T 29/49865; Y10T 29/49913
See application file for complete search history.

(56) References Cited

U.S. PATENT DOCUMENTS 5,836,965 A    11/1998    Jendersee et al.
5,913,871 A    6/1999    Werneth et al.
(Continued)

FOREIGN PATENT DOCUMENTS

EP              1 295 570        3/2003
WO          WO 99/55406       11/1999
(Continued)

*Primary Examiner* — Jermie Cozart
(74) *Attorney, Agent, or Firm* — Squire Patton Boggs (US) LLP

(57) ABSTRACT

A medical device-includes a polymer scaffold crimped to a catheter having an expansion balloon. The scaffold is crimped to the balloon by a process that includes inflating the delivery balloon during a diameter reduction to improve scaffold retention. A crimping temperature is maintained at about the onset of glass transition of the polymer material to facilitate more rapid stabilization of mechanical properties in the scaffold following crimping.

21 Claims, 3 Drawing Sheets

Related U.S. Application Data continuation of application No. 13/107,666, filed on May 13, 2011, now Pat. No. 8,752,265.

(51) Int. Cl.

| | | |
|---|---|---|
| *A61F 2/958* | (2013.01) | |
| *A61L 31/06* | (2006.01) | |
| *A61L 31/16* | (2006.01) | |
| *A61M 25/10* | (2013.01) | |
| *B29D 23/00* | (2006.01) | |
| *A61F 2/95* | (2013.01) | |
| *B29K 67/00* | (2006.01) | |

(52) U.S. Cl.
CPC . *B29K 2995/0082* (2013.01); *Y10T 29/49865* (2015.01); *Y10T 29/49913* (2015.01); *Y10T 29/49925* (2015.01); *Y10T 29/49927* (2015.01); *Y10T 29/49929* (2015.01)

(56) References Cited

U.S. PATENT DOCUMENTS

| | | |
|---|---|---|
| 5,976,181 A | 11/1999 | Whelan et al. |
| 6,629,350 B2 | 10/2003 | Motsenbocker |
| 6,666,880 B1 | 12/2003 | Chiu et al. |
| 6,745,445 B2 | 6/2004 | Spilka |
| 6,863,683 B2 | 3/2005 | Schwager et al. |
| 7,010,850 B2 | 3/2006 | Hijlkema et al. |
| 7,316,148 B2 | 1/2008 | Asmus et al. |
| 7,761,968 B2 | 7/2010 | Huang et al. |
| 7,951,185 B1 | 5/2011 | Abbate et al. |
| 8,002,817 B2 | 8/2011 | Limon et al. |
| 8,123,793 B2 | 2/2012 | Roach et al. |
| 8,261,423 B2 | 9/2012 | Jow et al. |
| 8,539,663 B2 | 9/2013 | Wang et al. |
| 8,595,913 B2 | 12/2013 | Knott et al. |
| 8,752,265 B2 * | 6/2014 | Wang ............... A61L 31/06 29/447 |
| 8,752,266 B2 * | 6/2014 | Jow ............... B29C 65/72 29/447 |
| 9,032,607 B2 * | 5/2015 | Jow ............... B29C 65/72 29/447 |
| 2002/0143382 A1 | 10/2002 | Hijlkema et al. |
| 2004/0078953 A1 | 4/2004 | Spilka |
| 2004/0106973 A1 | 6/2004 | Johnson |
| 2005/0119720 A1 | 6/2005 | Gale et al. |
| 2005/0143752 A1 | 6/2005 | Schwager et al. |
| 2006/0047336 A1 | 3/2006 | Gale et al. |
| 2007/0006441 A1 | 1/2007 | McNiven et al. |
| 2007/0271763 A1 | 11/2007 | Huang et al. |
| 2007/0282433 A1 | 12/2007 | Limon et al. |
| 2007/0289117 A1 | 12/2007 | Huang et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0147164 A1 | 6/2008 | Gale et al. |
| 2008/0275537 A1 | 11/2008 | Limon |
| 2009/0001633 A1 | 1/2009 | Limon et al. |
| 2009/0088829 A1 | 4/2009 | Wang et al. |
| 2009/0105800 A1 | 4/2009 | Sabaria |
| 2010/0004735 A1 | 1/2010 | Yang et al. |
| 2010/0025894 A1 | 2/2010 | Kleiner et al. |
| 2010/0063571 A1 | 3/2010 | Roach et al. |
| 2010/0323091 A1 | 12/2010 | Castro et al. |
| 2011/0270383 A1 | 11/2011 | Jow et al. |
| 2011/0271513 A1 | 11/2011 | Wang |
| 2012/0010693 A1 | 1/2012 | Van Sciver |
| 2012/0042501 A1 | 2/2012 | Wang et al. |
| 2012/0079706 A1 | 4/2012 | Knott et al. |

FOREIGN PATENT DOCUMENTS

| | | |
|---|---|---|
| WO | WO 2007/146354 | 12/2007 |
| WO | WO 2010/151497 | 12/2010 |

\* cited by examiner

METHODS FOR CRIMPING A POLYMERIC SCAFFOLD TO A DELIVERY BALLOON AND ACHIEVING STABLE MECHANICAL PROPERTIES IN THE SCAFFOLD AFTER CRIMPING

This application is a divisional of U.S. application Ser. No. 14/263,961 filed Apr. 28, 2014 now U.S. Pat. No. 9,155,870 B2, which is a continuation of U.S. application Ser. No. 13/107,666 filed May 13, 2011 now U.S. Pat. No. 8,752,265 B2, the entire contents of which are hereby incorporated by reference in its entirety for all purposes.

BACKGROUND OF THE INVENTION

Field of the Invention

The present invention relates to drug-eluting medical devices; more particularly, this invention relates to processes for crimping a polymeric scaffold to a delivery balloon.

Background of the Invention

The art recognizes a variety of factors that affect a polymeric scaffold's ability to retain its structural integrity when subjected to external loadings, such as crimping and balloon expansion forces. These interactions are complex and the mechanisms of action not fully understood. According to the art, characteristics differentiating a polymeric, bio-absorbable scaffolding of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing portion of a balloon-expandable scaffold (hereinafter "scaffold"). The models are not generally capable of providing an acceptable degree of certainty required for purposes of implanting the scaffold within a body, or predicting/anticipating the empirical data.

Moreover, it is recognized that the state of the art in medical device-related balloon fabrication, e.g., non-compliant balloons for scaffold deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed scaffold. One difference, for example, is the propensity for fracture or cracks to develop in a scaffold. The art recognizes the mechanical problem as too different to provide helpful insights, therefore, despite a shared similarity in class of material. At best, the balloon fabrication art provides only general guidance for one seeking to improve characteristics of a scaffold.

Polymer material considered for use as a scaffold, e.g. PLLA or PLGA, may be described, through comparison with a metallic material used to form a scaffold, in some of the following ways. A suitable polymer has a low strength to weight ratio, which means more material is needed to provide an equivalent mechanical property to that of a metal. Therefore, struts must be made thicker and wider to have the strength needed. The scaffolding also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA.

Processing steps performed on, design changes made to a metal stent that have not typically raised concerns for, or require careful attention to unanticipated changes in the average mechanical properties of the material, therefore, may not also apply to a scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping. As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different scaffold designs for improvement thereof, there are far less inferences, theories, or systematic methods of discovery available, as a tool for steering one clear of unproductive paths, and towards more productive paths for improvement, than when making changes in a metal stent.

It is recognized, therefore, that, whereas inferences previously accepted in the art for stent validation or feasibility when an isotropic and ductile metallic material was used, such inferences would be inappropriate for a scaffold. A change in a scaffold pattern may affect not only the stiffness or lumen coverage of the scaffold in its deployed state supporting a lumen, but also the propensity for fractures to develop when the scaffold is crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a scaffold that is plastically deformed, both when crimped to, and when later deployed by a balloon, unfortunately, is not as easy to predict as a metal stent. Indeed, it is recognized that unexpected problems may arise in scaffold fabrication steps as a result of a changed pattern that would not have necessitated any changes if the pattern was instead formed from a metal tube. In contrast to changes in a metallic stent pattern, a change in a scaffold pattern may necessitate other modifications in fabrication steps or post-fabrication processing, such as crimping and sterilization.

One problem frequently encountered with a scaffold for delivery to a site in a body using a balloon is reliably retaining the scaffold on the balloon as it passes through tortuous anatomy. If the scaffold is not held on the balloon with sufficient force, it can slip off of the balloon during transit to the target site. For a metallic stent, there are several approaches proposed for increasing the retention of the stent to a balloon during transit to the target site. However, methods proposed thus far for retaining the scaffold on a balloon are in need of improvement.

In one example of a method for crimping a metallic stent to a delivery balloon, the stent is placed in a crimper and the temperature elevated to facilitate greater compliance in the balloon material to allow material to extend between gaps in the stent struts. Additionally, balloon pressure is maintained while the stent is being crimped to increase stent retention to the balloon. After an initial pre-crimp, the stent is placed on the delivery balloon and allowed to slightly recoil under balloon pressure and while the stent has an elevated temperature. After this step, the stent is crimped onto the balloon while the balloon is pressurized. The stent is cycled to larger and smaller diameters. Additionally, balloon pressure may be supplied in bursts or held constant during these crimping steps. Further details of this process may be found in U.S. application Ser. No. 12/895,646 filed Sep. 30, 2010.

In light of the foregoing problems, there is a need for improving the retention of a scaffold on a balloon while avoiding adverse effects on the mechanical characteristics of the scaffold when the scaffold is fully deployed to support a lumen.

SUMMARY OF THE INVENTION

It has been found that the retention force of a crimped polymer scaffold on a delivery balloon may be increased by a process that includes crimping the scaffold to the balloon while the balloon is pressurized; that is, the balloon is pressurized at the same time as the scaffold's diameter is being reduced by crimper blades. Additionally, it has been found that if a crimping temperature is raised to about the onset of the glass transition temperature (TG) for the polymer, or slightly higher than this temperature, the stress relaxation period following crimping can be reduced significantly over previous methods that had crimped at temperatures below TG.

A crimping method according to the invention includes several crimping steps. For each crimping step where the scaffold is reduced in diameter, a balloon pressure is applied to support the scaffold during the diameter reduction and to work balloon material between scaffold struts. Following these crimping steps, a dwell period occurs in which balloon pressure is maintained to correct any misalignments in scaffold struts, deter further misalignment in subsequent crimping steps, and further work the balloon material between scaffold struts. The dwell period also serves to cause stress relaxation in the viscoelastic material. After one or more initial crimping steps, the partially-crimped scaffold is removed from the crimper head to check alignment on the balloon. This step is referred to as a final alignment, or check of final alignment step in the disclosure. After checking final alignment, the scaffold is returned to the crimper to perform the final crimp. The final diameter reduction is also performed with balloon pressure to urge balloon material between gaps in the scaffold struts before reaching the final crimped diameter. It was found that there was a significant increase in the retention or pull-off force of the crimped scaffold on the balloon when the balloon was pressurized during the crimping steps, i.e., when the scaffold diameter was reduced in size.

It had been previously believed that a crimping temperature for crimping a polymeric scaffold to a balloon should be a temperature slightly less than TG. However, at this temperature the stresses built-up in the crimped scaffold can take quite a long time (e.g., up to several weeks) to resolve, i.e., stress relaxation, for room temperature storage conditions after crimping. This results in varying mechanical properties in the scaffold, e.g., radial strength, for a period of time until the mechanical properties arrive at their final state. Differences in mechanical properties for deployed scaffolds subject to radial strength tests, e.g., 3 days verses two months, from crimping were observed. This needs to be improved. Scaffolds should have the same deployed properties whether they are deployed, e.g., 3 days or two months from crimping, for product reliability. It is therefore desired to have mechanical properties of crimped scaffold stabilize during a final dwell period of the crimping process, or soon after crimping is complete. The crimping temperature, however, should also not be raised too high to suit this need, because if raised too high memory loss in the material occurs during crimping that causes a loss in radial strength and/or fracture when the scaffold is deployed.

In accordance with these objectives, the invention seeks to both increase a retention force between a balloon and scaffold and reduce the stress relaxation period following crimping by selection of a crimping temperature of about the onset of TG, or slightly above this temperature, but without adversely affecting the scaffold mechanical properties during the crimping process. The material may be a polymer comprising PLLA or PLGA. It has been found that a crimping temperature suited to this purpose is the onset of TG (TG-low) or 5 degrees centigrade above the onset of TG. For this temperature range the stress relaxation due to large deformation caused by crimping would be greatly accelerated, thereby reducing the period of time it takes for radial strength, recoil and other important scaffold properties to stabilize. Thus, the time period from crimping to when scaffold properties stabilize is favorably reduced.

In another aspect of the invention, a scaffold is reduced in diameter by a factor of at least 2.5 when crimped and has a retention force of above 1.0 lb. The crimping process includes pressurizing the balloon both before and after the scaffold diameter is reduced by about 50% from its pre-crimp diameter.

In another aspect of the invention, the balloon pressure during dwell periods prior to a final alignment is about twice the balloon pressure applied after final alignment.

According to another aspect of the disclosure, a first crimping amount occurs before removing the scaffold to check alignment and a second crimping amount occurs after alignment. Greater balloon material can be urged between scaffold struts when the scaffold has a larger diameter; however, when at larger diameters the scaffold tends to move about more over the balloon. According to this aspect of the invention, the first and second amount of crimping are selected, in part, to crimp the scaffold sufficiently to enable adjustment of scaffold alignment on the balloon to achieve final alignment so that it will not shift on the balloon while leaving sufficiently-sized gaps between struts so that balloon material may be urged into gaps during the final crimp to increase scaffold retention force. In one embodiment the scaffold is reduced in diameter by about 50%, and then removed to check alignment. Then the scaffold is crimped by an additional about 33% to arrive at a final crimped diameter. The tube forming the scaffold has a diameter at about a deployed size or greater than a deployed size in this embodiment. For scaffold formed from a tube having a diameter less than or greater than a deployed size, each having the same final crimp size, the about 50% reduction may be correspondingly less than 50% or greater than 50%, respectively.

According to one embodiment, the ratio of diameter reduction before final alignment to the diameter reduction after final alignment may be about 1.5. For example, the scaffold diameter may be reduced by 50% before final alignment, and then reduced by 33% after final alignment.

The amount of diameter reduction for a single crimping step may be limited to no more than a 40% reduction in diameter, to allow for stress relaxation in the polymer material. The amount of diameter reduction and rate optimal for a scaffold will generally depend on the material and proximity to TG of the scaffold temperature during crimping. For example, the diameter reductions for a process that has three crimping steps may be about 20%, 40% and 30% for a PLLA scaffold and crimping temperature of about 58 Deg Celsius. The scaffold diameter may be initially reduced in size by 20%, followed by a dwell period, then the diameter is reduced in size by 38%, followed by a second dwell period, and then reduced to its final crimped diameter by reducing the diameter by an additional 33% where balloon pressure is supplied to increase scaffold retention during the final step. For these crimping percentages a 3.5 mm scaffold would be reduced in diameter size from 3.5 mm to 1.19 mm.

According to another aspect of the invention, a method for crimping a balloon-expanded scaffold to a balloon includes the steps of providing a tube comprising PLLA characterized by a glass transition temperature range having a lower limit of about TG-low; radially expanding the tube to increase its radial stiffness; forming the scaffold from the radially-expanded tube, including the steps of forming a circumferential series of closed cells having a W-shape and linear link struts connecting the W-shape cells; and crimping the scaffold to the balloon while the scaffold has a crimping temperature of between about TG-low and 5 degrees centigrade above TG-low including maintaining a pressure in the balloon as the scaffold diameter is being reduced in size.

According to another aspect of the invention, a method for securing a scaffold to a balloon includes the steps of crimping the scaffold to the balloon while the scaffold has a temperature of between about TG-low and 5 degrees centigrade above TG-low, the scaffold being made from a polymer comprising PLLA or PLGA, the crimping step including the steps of (a) reducing the scaffold diameter from a starting size to a first size while balloon pressure is at, or slowly reduced from a first pressure, e.g. 100 to 150 psi, while the diameter reduction occurs, (b) maintaining the first size for a first dwell period to allow for stress relaxation in the polymer, (c) reducing the scaffold diameter from the first size to a second size while balloon pressure is at, or slowly reduced from a first pressure, e.g. 100 to 150 psi, while the diameter reduction occurs, (d) maintaining the second size for a second dwell period to allow for stress relaxation in the polymer while the balloon has the first pressure, (e) reducing the scaffold diameter from the second size to a third size, (f) maintaining the third size for a third dwell period to allow for stress relaxation in the polymer while the balloon has the first pressure, and (g) reducing the scaffold diameter from the third size to a fourth size, wherein the balloon has a second pressure while the scaffold diameter is being reduced from the third size to the fourth size.

The scope of the methods and apparatus of the invention also encompass processes that may be used to crimp a scaffold as substantially described in US Pub. No. 2010/0004735 and US Pub. No. 2008/0275537. The thickness of the tube from which the scaffold is formed may have a thickness of between 0.10 mm and 0.18 mm, and more narrowly at or about 0.152 mm. The scaffold may be made from PLLA. And the scaffold may be crimped to a PEBAX balloon.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF EMBODIMENTS

Figure 1A:
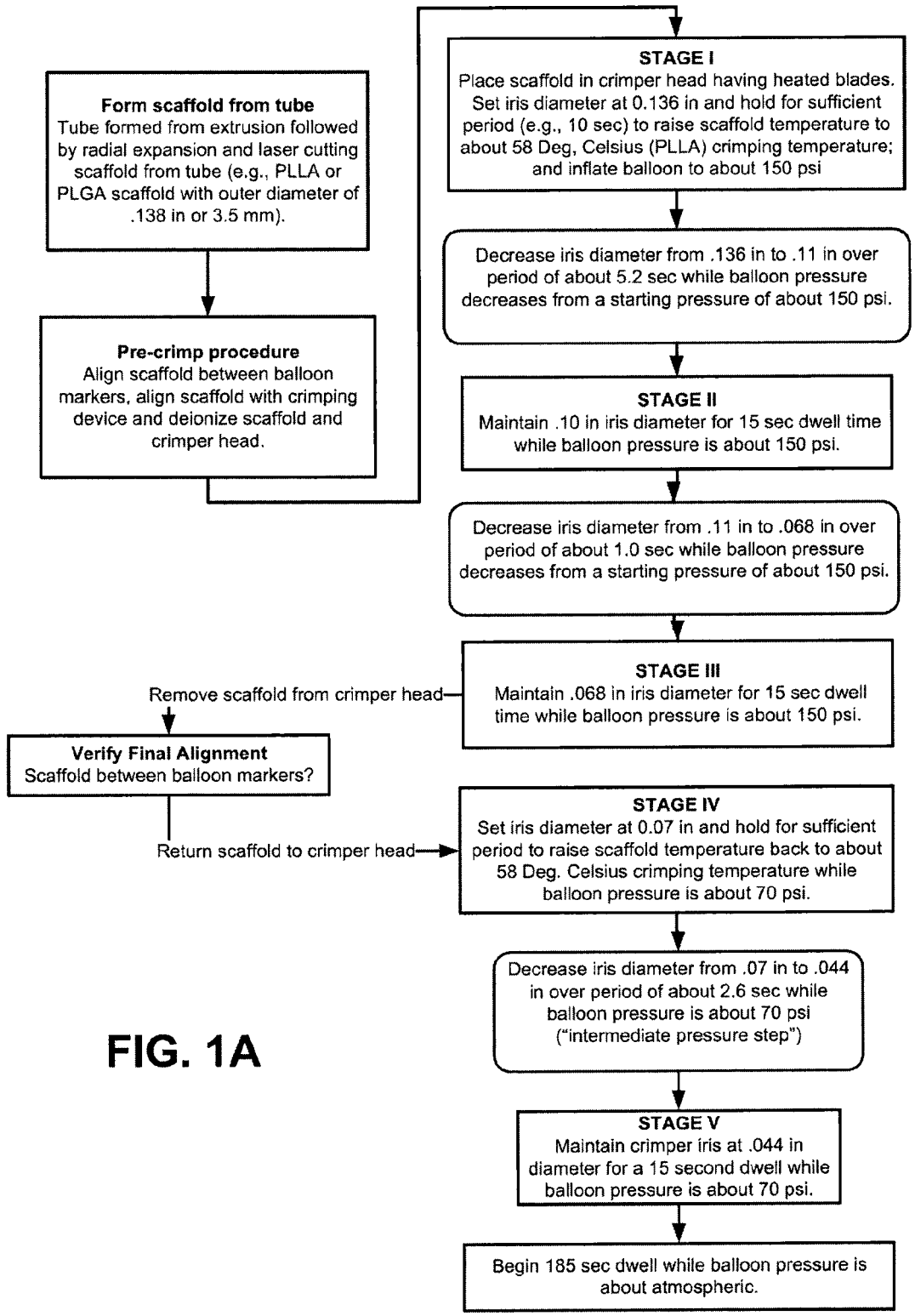
FIG. 1A shows a flow diagram for fabricating a scaffold and crimping the fabricated scaffold to a balloon according to the disclosure.

The "glass transition temperature," TG, is the temperature at which the amorphous domains of a polymer generally change from a brittle, vitreous state to a solid deformable or ductile state at atmospheric pressure. In other words, the TG corresponds to the temperature where the onset of noticeable segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. TG of a given polymer can be dependent on the heating rate and can be influenced by the thermal history of the polymer. Furthermore, the chemical structure of the polymer heavily influences the glass transition by affecting mobility.

Poly(lactide-co-glycolide) (PLGA) and Poly (L-lactide) (PLLA) are examples of a class of semi-crystalline polymers that may be used to form the scaffolds described herein. PLLA is a homopolymer and PLGA is a co-polymer. The percentage of glycolide (GA) in a scaffold constructed of PLGA may vary, which can influence the lower range of TG. For example, the percentage of GA in the matrix material may vary between 0-15%. For PLLA, the onset of glass transition occurs at about 55 degrees Celsius. With an increase of GA from about 0% to 15% the lower range for TG for PLGA can be correspondingly lower by about 5 degrees Celsius.

In one embodiment, a tube is formed by an extrusion of PLLA. The tube forming process described in US Pub. No. 2010/00025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the scaffold structural members cut from the tube without this expansion. The degree of radial expansion that the polymer tube undergoes characterizes the degree of induced circumferential molecular or crystal orientation. In a preferred embodiment, the radial expansion ratio or RE ratio is about 450% of the starting tube's inner diameter and the axial expansion ratio or AE ratio is about 150% of the starting tube's length. The ratios RA and AE are defined in US Pub. No. 2010/00025894.

The above scaffold's outer diameter may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the scaffold to dislodge in the vessel. Further, since a vessel wall cannot be assumed as circular in cross-section, and its actual size only an approximation, a physician can choose to over-extend the scaffold to ensure it stays in place. For this reason, it is preferred to use a tube with a diameter larger than the expected deployed diameter of the scaffold.

In one embodiment the ratio of deployed to fully crimped diameter is about 2.5. In this embodiment, the crimped diameter corresponds to an outer diameter that is only about 40% of the starting diameter. Hence, when deployed the drug eluting scaffold is expected to increase in size at least to about 2.5 times its crimped diameter size.

In one particular example, a scaffold is formed from a biaxially expanded tube having an outer diameter of 3.5 mm, which approximately corresponds to a deployed diameter (the scaffold may be safely expanded up to 4.0 mm within a lumen). The iris of the crimping mechanism reaches a diameter of 0.044 in, which is maintained for a 200 sec dwell period (i.e., scaffold held at 0.044 in outer diameter within crimping mechanism). When later removed from the crimper, the scaffold will recoil despite there being a restraining sheath placed over the scaffold immediately after the scaffold is removed from eth crimper. The scaffold and sheath are then subjected to radiation sterilization. At the point of use, i.e., at the point in time when a medical specialist removes the restraining sheath, the scaffold has an outer diameter of about 0.052 in (1.32 mm), or about 37% of the starting tube diameter of 3.5 mm. When in the crimping mechanism the scaffold reaches about 34% of the starting tube size.

As discussed earlier, fabrication of a scaffold presents challenges that are not present in metallic stents. One challenge, in particular, is the fabrication of a scaffold, which means the load bearing network of struts including connectors linking ring elements or members that provide the radial strength and stiffness needed to support a lumen. In particular, there exists an ongoing challenge in fabricating a scaffold that is capable of undergoing a significant degree of plastic deformation without loss of strength, e.g., cracks or fracture of struts. In the disclosed embodiments, a scaffold is capable of being deformed from a crimped diameter to at least 2.5 times the crimped diameter without significant loss of strength.

A problem encountered with fabrication of a scaffold for delivery to a site in a body using a balloon is the ability of the scaffold to be safely crimped to the balloon so that an adequate retention force is established between the scaffold and balloon. A "retention force" for a scaffold crimped to a balloon means the maximum force, applied to the scaffold along the direction of travel through a vessel that the scaffold-balloon is able to resist before dislodging the scaffold from the balloon. The retention force for a scaffold on a balloon is set by a crimping process, whereby the scaffold is plastically deformed onto the balloon surface to form a fit that resists dislodgment of the scaffold from the balloon. Factors affecting the retention of a scaffold on a balloon are many. They include the extent of surface-to-surface contact between the balloon and scaffold, the coefficient of friction of the balloon and scaffold surfaces, and the degree of protrusion or extension of balloon material between struts of the scaffold. As such, the pull off or retention force for a scaffold generally varies with its length. Therefore the shorter the scaffold the more likely it can become dislodged when the catheter is pushed through tortuous anatomy.

For a metal stent there are a wide variety of methods known for improving the retention force of a stent on a balloon via modification of one or more of the foregoing properties; however, many are not suitable or of limited usefulness for a scaffold, due to differences in mechanical characteristics of a scaffold verses a metal stent as discussed earlier. Most notable among these differences is brittleness of polymer material suitable for balloon-expanded scaffold fabrication, verses that of a metal stent, and the sensitivity of the polymer material to heat. Whereas a metal stent may be deformed sufficiently to obtain a desired retention force, the range of deformation available to a polymer scaffold, while avoiding cracking or fracture-related problems, by comparison, is quite limited. The application of heat has been shown as effective for increasing retention forces for metal stents. However, the heat levels used can cause detrimental effects to the polymer material since they tend to correspond to temperatures well within, or above the TG of the material. For this reason, known heat methods for increasing retention forces for metal stents tend to be viewed as inappropriate for increasing a retention force between a scaffold and balloon.

The invention addresses the unique challenges presented by a scaffold that needs to be retained on a balloon. These challenges are present for several reasons. First, there is less space available between struts in a crimped state, which prevents balloon material from extending between struts. As a result, there is less abutment or interference between struts and balloon material, which interference/abutment has previously been relied upon to increase the retention force of a metal stent on a balloon. This condition is a result of the need to fabricate wider and thicker struts for the scaffold, as compared to a metal stent, so as to provide adequate, deployed radial strength. Second, as indicated above, a polymer is more sensitive to temperature ranges that have previously been used to increase retention to a balloon. Heating of a scaffold too high relative to its TG induces significant changes in the molecular orientation of the polymer material that result in loss of strength when the scaffold is plastically deformed to its deployed diameter.

The art has previously devised methods for retaining a scaffold on a delivery balloon in response to these challenges. In one example, the scaffold is crimped to the delivery balloon at a temperature well below the polymer's TG. Then the scaffold, disposed between ends of the balloon, is thermally insulated from the balloon's ends. The ends of the balloon are then heated to about 185 degrees Fahrenheit to expand the diameter of the balloon material at its ends. The expanded balloon ends form raised edges abutting the scaffold ends to resist dislodgment of the scaffold from the balloon. In one example, this process provided a retention force of about 0.35 lb. for a Poly (L-lactide) (PLLA) scaffold crimped to a polymide-polyether block co-polymer (PEBAX) balloon. An example of this process is disclosed in U.S. Pat. No. 6,666,880.

U.S. patent application Ser. No. 12/772,116 filed Apr. 30, 2010 ("'116 application) discusses a study that was conducted to investigate the effects on retention forces for crimped scaffolds. Principally, this study identified a temperature range relative to a TG of the scaffold material that improved retention forces without detrimentally affecting scaffold mechanical properties when deployed to support a vessel. For PLLA it was found that modifying the pressure and hold time of the scaffold for crimping temperatures of between 40° and 55° C. improved the scaffold retention, with about 45-51° C. and 48° C. being preferred temperatures for a PLLA scaffold. Additionally, the '116 application found that retention forces could be improved if the scaffold were crimped down to an intermediate diameter and then the balloon is deflated then re-inflated, followed by crimping the scaffold down to a final crimp diameter. The '116 application also contemplates similar results for PLGA, if TG for this material is taken into consideration and assuming other characteristics of the process and scaffold pattern. For PLGA having % GA of about 5% the temperature ranges for crimping may be between about 46 to 53 degrees Celsius. For PLGA having % GA of about 15% the temperature ranges for crimping are about 43 to 50 degrees Celsius.

When the scaffold is crimped to a balloon while being heated to temperatures well within the range of TG for the scaffold polymer, there is a greater tendency for polymer chain re-alignment to occur that will result in loss of strength when the scaffold is later deployed. Unacceptable crack formation (either in the number or extent of cracks), voids or outright fracture was observed in subsequent testing. If the crimping temperature is raised too high relative to the TG of the polymer, the memory of the matrix material at the starting tubing diameter is being removed, or reformed as the scaffold is deformed. As a consequence, when the scaffold is later expanded under physiological conditions, e.g., body temperature; it becomes more susceptible to crack formation due to its brittle properties at body temperatures and lack of chain alignment from its starting diameter. Retention force and scaffold integrity when crimped to the balloon generally improves at higher temperatures, however, the scaffold loses its structural integrity when later deployed if the temperature is raised too high, e.g., above TG. On the other hand, when the scaffold is heated to temperatures below about 15 degrees Celsius of the glass transition temperature, or not heated at all, there is no noticeable improvement in scaffold retention. The '116 application states, based on the tests conducted, that the most effective range was between about 15 degrees below and up to about TG.

The '116 application explains that the above and related unexpected results may be explained in the following manner. When a polymer scaffold is crimped at a temperature slightly below its TG (e.g., from 5 to 15 degrees Celsius below TG), there are very short chains of the matrix material that are able to freely move to assist in the deformation of the scaffold without exceeding material stress limits. At the same time, the longer chains of the matrix substantially maintain their alignment, and, thus, stay intact without losing their orientation set when the starting tube was expanded. By doing so, the scaffold may be crimped down to a diameter for good scaffold retention, while the orientation of a majority of polymer chains would be the same to ensure desirable strength and fracture toughness in the final product, i.e., when the scaffold is deployed to support a vessel.

FIG. 1 of the '116 application shows a flow for a crimping process for a 3.0 mm (0.118 in) scaffold that is crimped to a final crimp diameter of 0.044 in. The diameter reduction from 0.118 in to 0.044 in includes three intermediate crimping diameters of 0.083 in, 0.063 in and 0.07 in, following a "pre-crimp" procedure in which the PLLA scaffold temperature is raised to a temperature of about 48° C. When the scaffold has attained the intermediate crimp diameters, the crimper jaws are held at the crimping diameter for a dwell period of 30 sec, 15 sec and 10 sec, respectively. After the final crimp diameter has been obtained, the crimp jaws are held at the final crimp diameter for about 200 sec. The delivery balloon, i.e., a PEBAX balloon, is inflated to a pressure of 17 psi for the dwell period 30, 15 and 10 second dwell periods. The dwell periods for the intermediate crimping stages are included in the process to allow for stress relaxation in the polymer material before decreasing the scaffold diameter further. Before the crimper iris is reduced by actuation of the crimper jaws, the balloon is deflated. Thus, in a preferred embodiment of the '116 application whenever the scaffold diameter is decreased, the balloon is not inflated. Additionally, according to the '116 application a preferred temperature for crimping is about 48° C.

Notwithstanding improved results in stent retention when practicing inventions described in the '116 application, it is desirable to further increase a scaffold retention force. For example, for a coronary scaffold it is desirable to have a balloon-scaffold retention force (i.e., force required to pull scaffold off balloon) of at least 0.7 lbs and preferably over 1.0 lbs. According to the disclosure, methods of the invention are expected to increase the retention force on an 18 mm length, 3.5 mm pre-crimp diameter scaffold by at least 0.5 lbs over the process used to produce the data in the '116 application. As explained in greater detail below, it was found that modification of the balloon pressure during various stages of the crimping process can improve retention forces.

Additionally, it has been recently discovered that when crimping to temperatures of below TG, e.g., 48° C. for a PLLA scaffold, the stress relaxation within the material is not resolved within a reasonable period of time following crimping. In subsequent testing of crimped polymer scaffold one, two, or three months from the time of crimping it was found that mechanical properties such as the radial strength of the scaffold vary depending on when the scaffold was deployed from the balloon following crimping. There was a drop in radial strength when stress relaxation occurred. For example, when a first scaffold was deployed by the balloon three days after crimping, the first scaffold exhibited a lower radial strength than a second scaffold, crimped in the same way, that was deployed by the balloon one month after crimping.

For commercial production of a scaffold-balloon catheter consistent properties of the final product, whenever it is used, is essential. It is desirable, therefore, to have a crimping process such that the mechanical properties of the scaffold upon deployment will be consistent, regardless of when the scaffold is used following crimping. Scaffold use, for example, may be within a few days, months, or even a year after crimping. Thus, it is desirable, from a commercial production standpoint, for the scaffold-balloon catheter assembly to have stable mechanical properties within a short period after crimping.

More stable mechanical properties of the scaffold shortly following crimping are possible if a higher crimping temperature is used. When the crimping temperature is raised, polymer chains within the scaffold can more easily move about, which translates into reduced internal stresses in the material during the crimping process. As such, the period of time needed for stress relaxation following crimping should be less when a higher crimping temperature is used. However, there is a tradeoff between greater mobility during crimping and memory loss in the material. If the temperature is raised too high, the crimping of the heated scaffold will induce polymer chains to re-align to such an extent that the desirable pre-crimp alignment of chains in the circumferential direction will be lost. This results in a loss in radial strength, and/or strut fractures in the deployed scaffold.

The inventor found that if the scaffold temperature is raised to, or slightly above the initiation of glass transition in the material, the time needed for mechanical properties to stabilize (i.e., the stress relaxation period) can be significantly reduced while retaining good structural integrity and radial strength in the deployed scaffold. For a PLLA scaffold this temperature is between about 55° C. and 60° C. or more preferably between about 58° C. and 60° C.

For a PLGA scaffold this temperature can vary depending on the percentage of glycolide (GA) in the material. For example, the percentage of GA in the matrix material may vary between 0-15%. With an increase of GA from about 0% to 15% the lower range for TG for PLGA can be correspondingly lower by about 5° C. Thus, for a PLGA scaffold having 15% GA the temperature that helps stabilize mechanical properties within a shorter time period following crimping is between about 50° C. and 55° C. or more preferably between about 53° C. and 55° C.

Figure 1B:
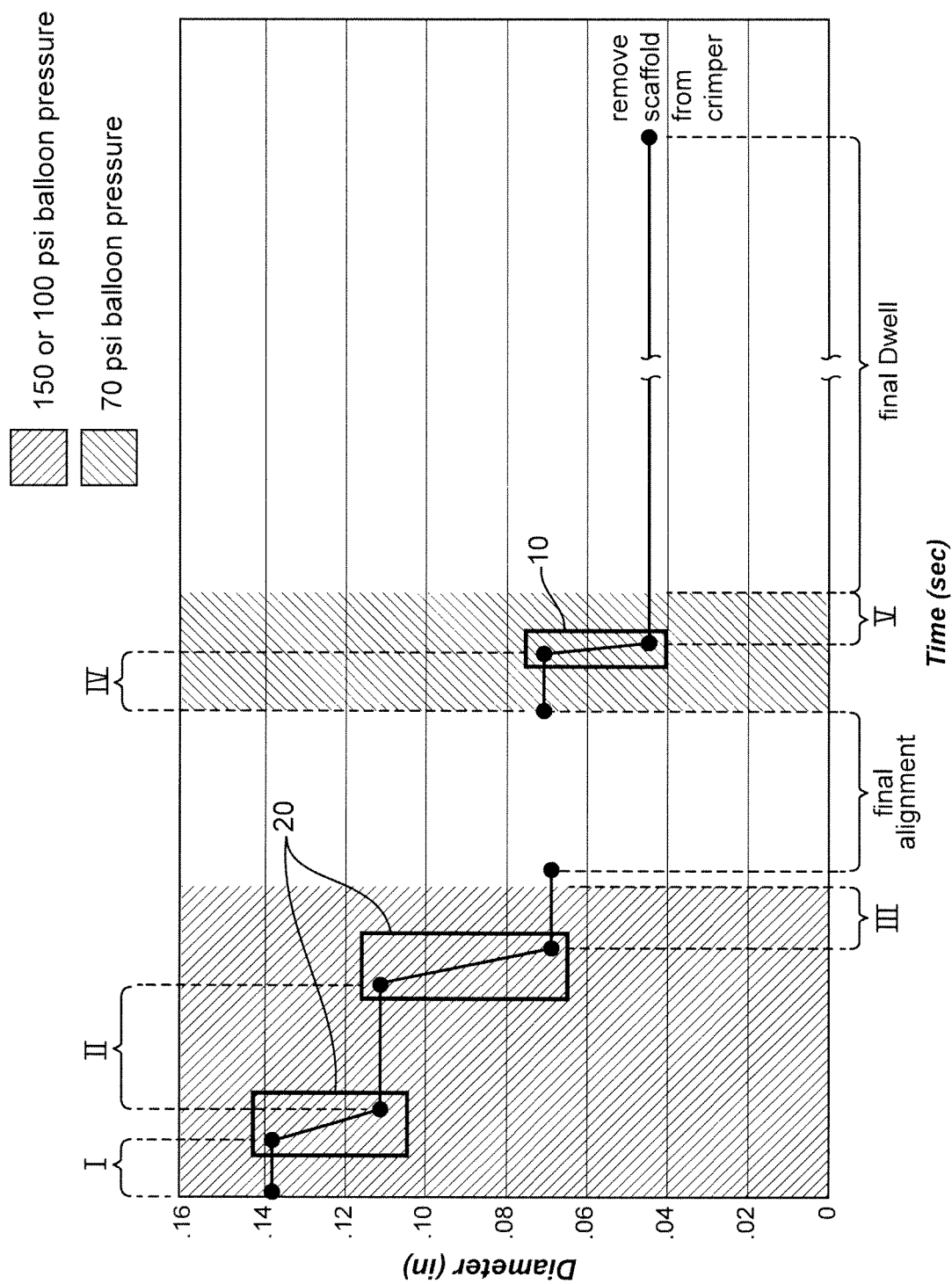
FIG. 1B shows the crimping process portion of FIG. 1A in graphical form, plotting scaffold diameter vs. time and indicating the balloon pressure supplied during steps of the crimping process.

Referring to FIGS. 1A-1B there is a flow process and graph, respectively, of a crimping method for a 3.5 mm diameter and 18 mm length scaffold. The method is discussed herein as a series of five "stages" with diameter reduction steps between stage. Each "stage" refers to a period where the crimper jaws are maintained at a constant diameter for a dwell period. The scaffold diameter is constant during these periods.

For the stages preceding the "final alignment" or "verify final alignment" step in FIGS. 1A-1B, where the scaffold and balloon are removed from the crimper to check alignment, the balloon is inflated to minimize further out of plane, or irregular movement or twisting of struts initiated in preceding crimping steps during subsequent crimping steps. Some of the advantages of inflating a balloon during these dwell periods to achieve this result are explained in U.S. application Ser. No. 12/861,719 filed Aug. 23, 2010. Additionally, it is believed that by supplying a balloon pressure during both the periods of diameter reduction as well as during dwell periods (stages) preceding final alignment, balloon retention can improve.

As mentioned earlier, a polymer scaffold, and in particular a misaligned polymer scaffold is more susceptible to damage within a crimper than a corresponding metal stent. A polymer scaffold that has even a "slight" misalignment within the crimper has a far greater chance of becoming damaged than a metal stent. Of course, the need to avoid twisting or bending in struts of metal stents when in a crimper is known. However, unlike metal stents, which are far more tolerant of local irregular or non-uniform forces acting on struts through blade edges, polymer struts are more easily distorted when the crimping forces are non-uniformly applied. Due to the proximity of struts to each other (as required since thicker and wider struts are needed to provide equivalent stiffness to a metal stent and there is sometimes a greater diameter reduction needed during crimping), there is a greater chance of abutting struts which leads to out of plane twisting and overlapping scaffold structure in the crimped state. The effects of irregular or non-uniform crimping forces on a polymer scaffold are therefore more severe than in the case of a metal stent. The differences are most clearly evident in the instances of cracking and/or fracture in deployed polymer scaffolds that show irregular twisting or bending.

Local, luminal-side support for individual struts during the dwell periods is believed to correct for struts predisposed to twist or overlap with adjacent struts (a strut predisposed to twist or overlap with other struts refers to a strut that was previously slightly bent or twisted out of plane when the scaffold was at a larger diameter). In essence, balloon pressure during the dwell periods is believed to apply a beneficial correcting force on the luminal side of struts, which can serve to limit a strut's potential to overlap or twist further as crimper blades are applied in subsequent steps. If balloon pressure is also supplied during the diameter reduction steps as described in FIGS. 1A-1B, initiation of twisting or overlapping of struts can be deterred by the supporting balloon material.

If crimped down from a larger diameter and in the absence of supporting balloon pressure, there is little if any stabilizing support available for the scaffold since its diameter is much larger than the deflated balloon upon which the scaffold sits. As such, any initial non-uniform applied crimping force, or misalignment, e.g., due to a residual static charge on the polymer surface, can initiate irregular bending that becomes more pronounced when the scaffold diameter is reduced further. Friction between the blades and the scaffold surface, or residual static charge or static charge buildup induced by sliding polymer surfaces are also suspect causes of this irregular deformation of the scaffold. When the balloon is inflated to support the scaffold from the interior during dwell and diameter reduction periods, the irregular bending and twisting of struts seen at the final crimp diameter (when the scaffold is removed from the crimper) are reduced substantially. The scaffold is more able to maintain a proper orientation with respective to the crimper axis when the balloon is supporting the scaffold at large scaffold diameters. Preferably, the balloon pressure is held constant during the pre-final alignment dwell periods (Stage I, II and III) and gradually reduced, or allowed to reduced from a starting pressure to an end pressure during the diameter reduction steps occurring between Stage I and II and II and II in FIGS. 1A-1B.

The scaffold is partially crimped, then removed from the crimper to check its alignment on the balloon (Stages I, II, III as the dwell periods). The scaffold is then returned to the crimper to perform final crimp steps, e.g., Stage IV, reduce to 0.044 in, then dwell Stage V. During these final steps the balloon is approximately at a constant pressure. The presence of balloon pressure during the final crimp (the "intermediate pressure" step), as compared to the same process without the "intermediate pressure" step, i.e., about atmospheric balloon pressure for the final crimp, greatly increases the retention force of the scaffold to the balloon. Stated differently, the retention force of scaffold to balloon was much higher when the balloon is pressurized during the final crimp, or diameter reduction step.

It is believed that the greatly increased retention force was achieved because the balloon material opposing gaps in scaffold struts during the final crimp tended to extend in-between gaps more often as the scaffold was crimped due to the opposing balloon pressure applied to the balloon material. Without this pressure, the balloon material tended to deflect away from the gaps as the size of the gaps narrowed during the final crimp. Essentially, the balloon pressure forced more balloon material into gaps—rather than deflect the material away from the gaps—when the diameter is being reduced in size.

The balloon pressure supplied prior to final alignment is also believed to contribute to an increased retention force. Since the scaffold and balloon may sometime need re-alignment before the final crimp, any balloon movement between struts prior to final alignment would seem to not contribute much to the retention force between balloon and scaffold (since when the scaffold is moved over the balloon to re-align it, any balloon material disposed to extend through a space between struts—thereby resulting in more material between struts during final crimp for increased retention force —would be shifted away from this space when the scaffold was re-aligned with respect to the balloon). When the balloon pressure is supplied during the diameter reduction steps and stages preceding final alignment, however, the balloon material is worked between the spaces, in essence, making the material more predisposed to extend through the spaces. Since the spaces are larger before final alignment, more of the balloon material can be worked between the spaces. And although the space opposing balloon material may change during final alignment, this working of balloon material prior to final alignment should facilitate greater penetration between struts during the final crimp (Stages IV, V and the intermediate pressure step) than if the balloon pressure was not supplied for the steps preceding final alignment.

The working of balloon material referred to above, in order to make it more capable of protruding between gaps, can be understood by reference to the starting configuration of the balloon. Non-compliant balloons typically have tightly-folded wings so that the balloon has a small crossing profile. If the scaffold is crimped to the balloon in this configuration, very little of the balloon material will extend between spaces. If the balloon is inflated when the scaffold is being crimped at the large diameters, i.e., between stages I and II, the folds can be substantially undone and balloon material allowed to more easily extend between spaces. Then in the final crimp steps, the balloon material is more pre-disposed to extend between spaces. Prior to final alignment the balloon the balloon material is conformed to the architecture of the scaffold, more or less, so that during the final step with the intermediate pressure supplied, the balloon is more likely to extend between spaces. A balloon-inflation step during crimping to undue balloon folds is also described in US 2009/0088829.

EXAMPLES

Further details of the FIG. 1A flow process for a 3.5 mm scaffold manufacture and crimping to a delivery balloon will now be discussed. FIG. 1B illustrates in graphical form the crimping portion of the FIG. 1A flow—a graph of scaffold diameter verses time with a balloon pressure of 150 psi or 70 psi applied during the dwell periods and the intermediate pressure step (i.e., crimping between Stage IV and Stage V). The scaffold was crimped using a crimper having film-sheets disposed between the metal crimper blades and the scaffold. This particular type of crimper is discussed in greater detail below.

As discussed above, the scaffold is formed from a PLLA or PLGA precursor, including a biaxial expansion of the precursor to form a tube, followed by laser cutting the scaffold from the tube. Next, a pre-crimp procedure is performed, which includes placing the scaffold between the balloon markers and aligning the scaffold with the iris of the crimper. Using an anti-static air gun, both the scaffold and interior of the iris chamber are deionized. The deionization step was found necessary to reduce misalignments of the scaffold resulting from a static charge buildup caused by sliding contact between polymer surfaces, as explained in more detail in U.S. application Ser. No. 12/776,317 filed May 7, 2010 (62571.398).

Stage I:

The scaffold (supported on the balloon of the balloon-catheter) is placed within the crimp head. The crimping temperature is obtained by heating the crimper jaws to an appropriate temperature and then bringing the jaws into thermal contact with the scaffold. The crimper jaws are set to 0.136 in and maintained in this position for about 10 seconds to allow the scaffold temperature to increase to a crimping temperature that is near to the TG of the scaffold material (e.g., the crimping temperature for a PLLA scaffold of FIG. 1 is 58+/−3° C.). More generally, the scaffold temperature may be between about the onset of TG (i.e., the lower range of TG or TG-low) and about 5 degrees Celsius above TG-low for the polymer material. Whenever the scaffold is within the crimper head its temperature is at, or rises to the crimping temperature (e.g., 58+/−3° C.) for the crimping process described in FIGS. 1A-1B. The balloon is inflated to about 150 psi during Stage I.

After the scaffold reaches the crimping temperature, the iris of the crimper closes to reduce the scaffold diameter from 0.136 in (3.5 mm) to about 0.11 in, or about a 20% diameter reduction. During this diameter reduction step (Stage I→Stage II) the valve supplying pressure to the balloon is opened slightly to allow pressure reduction (pressure is bled from the valve) from its starting 150 psi pressure as the scaffold diameter is reduced in size. The about 20% reduction in diameter occurs over a period of about 5.2 seconds. As compared to subsequent diameter reduction steps, this diameter reduction is performed more slowly because strut angles are at their widest. It was found that a slow rate of diameter reduction can significantly improve yield, in terms of more uniformity of compression in the scaffold structure; that is, to enable the scaffold structure to compress more evenly, without irregular bending or twisting of strut and/or link structure. Further details on this aspect of the crimping process are described in U.S. application Ser. No. 12/861,719 filed Aug. 23, 2010. Moreover, during Stage I and this diameter reduction step balloon folds are undone and the material begins to conform to spaces between scaffold struts. By using a 150 psi balloon when the scaffold has the large 0.136 to 0.11 in diameter (compared to the balloon diameter), more balloon material can be worked into the spaces between struts, thereby making more of the balloon material capable of extending between struts at smaller diameters.

Stage II:

The crimper jaws are held at the 0.11 in diameter, the balloon pressure is re-set to about 150 psi, and the scaffold and balloon are maintained in this configuration for a 30 second dwell period at the crimping temperature. This period allows balloon material to further extend into, or conform to the spaces between scaffold struts. Moreover, by carrying out this step, and the other steps in the crimping process of FIG. 1A at the more elevated temperature of about 58° C. (compared to about 48° C. in the '116 application) the balloon-strut interaction is more extensive since the structure is at a higher temperature (balloon material is more compliant at the higher temperature).

After the 30 second dwell period is complete, the crimper iris is moved from 0.11 in to 0.068 in or about a 38% diameter reduction. During this second diameter reduction or crimp step (Stage II→Stage III) the balloon pressure is again allowed to reduce from 150 psi as the scaffold diameter is reduced further. This about 38% reduction in diameter occurs over a period of 1.0 second. The about 50% diameter reduction was found to achieve an acceptable balance between balloon-scaffold engagements while retaining an ability to re-align the scaffold in a final alignment step. If the scaffold is crimped too tightly before final alignment, then it becomes difficult to re-position it between balloon markers, should this be necessary. If crimped too loosely before final alignment, then the scaffold can shift after final alignment, e.g., if the balloon-scaffold is moved into the crimper head too quickly, the scaffold can slip on the balloon. It will be appreciated that this balance also should take into consideration the available spacing between struts for balloon material to extend into during the final crimp (if the spacing is too small after final alignment, then less balloon material can extend between struts during the final crimp).

Stage III:

The crimper jaws are held at the 0.068 in diameter, the balloon is again inflated or re-set to a pressure of 150 psi, and the scaffold and balloon maintained in this configuration for a 15 second dwell period at the crimping temperature to correct or counter any twisting or misalignment that might have developed when the scaffold diameter was reduced by about an additional 38%.

Final Alignment Step:

After the 15 second dwell period is complete, the scaffold and balloon are removed from the crimper to check the scaffold alignment on the balloon. This alignment involves a visual inspection and if necessary manual adjustment of the scaffold to place it between the balloon markers.

As mentioned earlier, the scaffold's starting or pre-crimp diameter is about equal to, or greater than the deployed diameter for the scaffold, which is between about 2.5 and 3.0 times its final crimped diameter. The expanded tube and pre-crimp scaffold diameter is 2.93 times the final-crimp size in the illustrated example. This difference in diameters between scaffold and balloon, coupled with the likelihood that crimper jaws will not apply a net-zero longitudinal force on the scaffold as the diameter is reduced, the scaffold will slip when being placed into the crimper, and/or that the scaffold will be slightly misaligned when it reaches the balloon surfaces, has lead to a need for verifying alignment of the scaffold on the balloon; that is, checking to see that the scaffold is located between balloon markers.

The additional, time-consuming alignment step that interrupts the crimping process is typically not required for a metal stent, for two reasons. First, the starting diameter for a metal stent is much closer to the final diameter, which means the balloon-stent interaction that holds the stent in place happens relatively quickly. Second, for higher crimping rates used for metal stents, there is usually less ability for the stent to shift longitudinally over the balloon surface. Metal stents can be crimped at relatively high rates, whereas crimp rates for polymer scaffolds generally should be monitored and often times reduced (from metal crimp rates) because a polymer scaffold's structural integrity in its crimped and deployed states is affected by the crimp rate. While metals exhibit rate independent material behavior, polymers are viscoelastic and exhibit rate dependent material response. Polymers subjected to higher strain or displacement rates will experience higher stresses and exhibit less ductility.

After Stage III the scaffold's diameter has been reduced to about ½ of its starting diameter. It was observed that not until the scaffold diameter was reduced to about 50% of its pre-crimp diameter size was the scaffold-balloon interaction sufficient to prevent longitudinal shifting of the scaffold on the balloon when the scaffold was crimped down further. In the example of FIG. 1, therefore, the final-alignment step is performed once the scaffold reaches about 50% of its pre-crimp diameter. The Stage III diameter of 0.068 in places the scaffold relatively close to the deflated balloon to hold it in place, but not too tightly on the balloon so as to prevent re-alignment with respect to the balloon alignment markers. When the scaffold and balloon are removed from the crimper to check alignment, the scaffold recoils from the balloon (e.g., from about 0.068 in to about 0.075 in).

Stage IV:

The scaffold and balloon are placed into the crimper. The jaws are closed to a diameter of 0.07 in and the balloon inflated to a pressure of 70 psi (the pressure used for the intermediate pressure step in this example). Thereafter the scaffold is crimped to its final crimp diameter of 0.044 in or about a 33% reduction in diameter over a period of about 2.6 seconds while balloon pressure is maintained at 70 psi. Before the final diameter reduction to 0.044 in commences, a dwell period of 10 seconds at the 70 psi balloon pressure is performed to allow time for the scaffold to return to the crimping temperature.

As illustrated in FIG. 1B, at the start of the Stage IV step the balloon pressure is set to 70 psi, and this setting is unchanged during the subsequent Stage IV dwell, the subsequent diameter reduction from 0.07 in to 0.044 in or about a 33% reduction ("intermediate pressure"), and the Stage V dwell. The pressure is not adjusted to maintain 70 psi; as such the balloon pressure is expected to change somewhat from 70 psi during the intermediate pressure step.

Stage V:

After the scaffold has been reduced in diameter from 0.07 in to 0.044 in the balloon pressure is maintained at 70 psi for a period of about 15 seconds.

Following Stage V dwell period, the balloon pressure is returned to about atmospheric pressure and the crimper jaws are held at the final crimp diameter for a 185 second dwell period. During this final dwell period the degree of recoil in the scaffold is reduced and stress relaxation is allowed to occur. Immediately following the 185 second dwell the scaffold is removed and a retaining sheath is placed over the scaffold to restrain any further possible recoiling of the structure.

The amount of balloon pressure applied during dwell periods and diameter reduction steps will of course need to take into account the stresses placed on the balloon. If balloon pressures are high, support from the balloon should be favorable and retention forces higher, but there is also increased risk of pin holes developing in the balloon. In the illustrated embodiment pressures of 150 psi and 70 psi are chosen, with balloon pressure being reduced during the pre-final alignment diameter reduction steps.

In another embodiment balloon pressure prior to final alignment may also be held constant. In this embodiment, is set at a constant, and allowed to increase as the scaffold diameter is reduced in size from Stage I to Stage III. Alternatively, the balloon pressure may be set at a pressure (e.g., 100 psi) at the initiation of a stage, and then not adjusted until after the subsequent diameter reduction. Thus, for example, balloon pressure is set at 100 psi at Stage I, then re-set at 100 psi at the start of Stage 2, etc.

Figure 2:
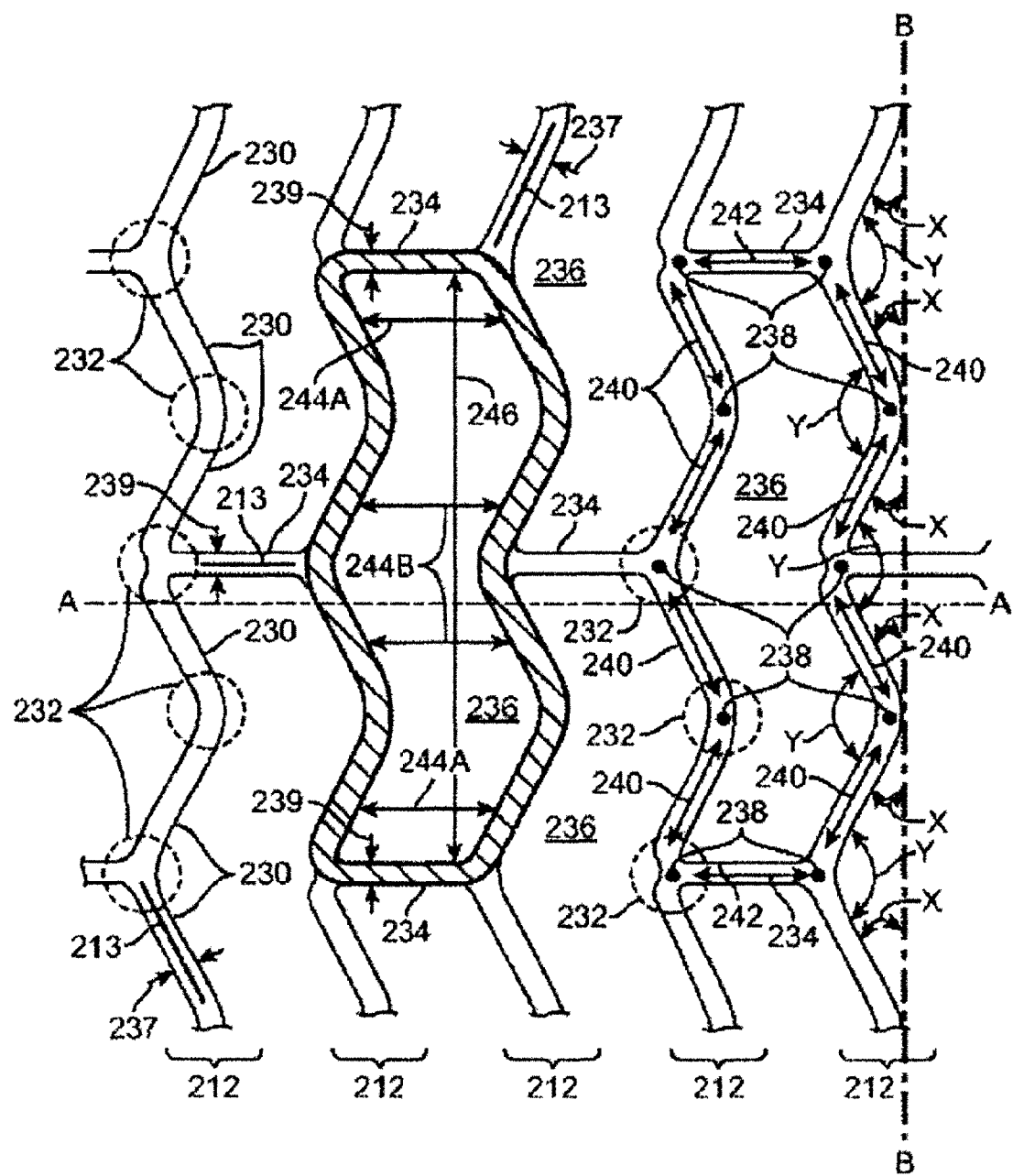
FIG. 2 is a planar view of a portion of a scaffold that was crimped to a balloon according to aspects of the disclosure. This view describes the scaffold pattern of the load-bearing structure of the scaffold that is crimped to a balloon according to the process of FIG. 1A-1B.

As noted above, in a preferred embodiment a scaffold has the pattern described in U.S. application Ser. No. 12/447,758 (US 2010/0004735) to Yang & Jow, et al. Other examples of scaffold patterns suitable for PLLA are found in US 2008/0275537. FIG. 2 of US 2008/0275537 shows a detailed view of an intermediate portion 216 of a strut pattern 200 depicted in US 2010/0004735. The intermediate portion includes rings 212 with linear ring struts 230 and curved hinge elements 232. The ring struts 230 are connected to each other by hinge elements 232. The hinge elements 232 are adapted to flex, which allows the rings 212 to move from a non-deformed configuration to a deformed configuration. Line B-B lies on a reference plane perpendicular to the central axis 224 depicted in US 2010/0004735. When the rings 212 are in the non-deformed configuration, each ring strut 230 is oriented at a non-zero angle X relative to the reference plane. The non-zero angle X is between 20 degrees and 30 degrees, and more narrowly at or about 25 degrees. Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the scaffold is deployed. Having the interior angle be less than 180 degrees allows the scaffold to be crimped while minimizing damage to the scaffold struts during crimping, and may also allow for expansion of the scaffold to a deployed diameter that is greater than its initial diameter prior to crimping. Link struts 234 connect the rings 212. The link struts 234 are oriented parallel or substantially parallel to a bore axis of the scaffold. The ring struts 230, hinge elements 232, and link struts 234 define a plurality of W-shape closed cells 236. The boundary or perimeter of one W-shape closed cell 236 is darkened in FIG. 2 for clarity. In FIG. 2, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

Referring to FIG. 2, the perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other. Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 of the strut pattern. The distances 242 are the same or substantially the same for each link strut 234. The ring struts 230 have widths 237 that are uniform in dimension along the individual lengthwise axis 213 of the ring strut. The ring strut widths 237 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness in the radial direction, which is between 0.10 mm and 0.18 mm, and more narrowly at or about 0.152 mm.

As shown in FIG. 2, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236.

It will be appreciated from FIG. 2 that the strut pattern for a scaffold that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the scaffold central axis. The link struts 234 are oriented parallel or substantially parallel to the scaffold central axis. The link struts 234 connect the rings 212 together. The link struts 234 and the ring struts 230 defining W-shape closed cells 236. Each W-shaped cell 236 abuts other W-shaped cells. The ring struts 230 and hinge elements 232 on each ring 212 define a series of crests and troughs that alternate with each other. Each crest on each ring 212 is connected by one of the link struts 234 to another crest on an immediately adjacent ring, thereby forming an offset "brick" arrangement of the W-shaped cells.

An iris-type crimper from Machine Solutions, Inc (MSI) was used to crimp the scaffold according to FIGS. 1-2. The crimper includes three rolls arranged to position a clean sheet of non-stick material between crimping blades and the scaffold prior to crimping. The sheet is drawn from the backing sheet by a rotating mechanism (not shown) within the crimper head. A second sheet is dispensed from a mid roll. After crimping, the first and second (used) sheets are collected by a lower roll. Within the iris two sheets are passed between two blades on opposite sides of the positioned scaffold and balloon, and a tension is applied to gather up excess sheet material as the iris of the crimping assembly is reduced in size via the converging blades. For the crimping process of FIGS. 1A-1B the scaffold is crimped using this type of crimper. As explained in U.S. application Ser. No. 12/861,719 filed Aug. 23, 2010 it was found that the polymer sheets disposed between the scaffold and crimper blades help to reduce indentations in scaffold surfaces since the polymer sheets effectively make the blade surfaces more compliant.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for making a medical device, comprising:
using a scaffold formed from a tube comprising a polymer, the scaffold having struts and an outer diameter, and the polymer is characterized by a glass transition temperature (Tg) having a lower limit (Tg-low);
using a crimping device having a crimp head, crimping the scaffold to a balloon of a balloon catheter to cause the scaffold's polymer struts to become pressed into a surface of the balloon by the crimp head and causing balloon material to extend into spaces between the struts as an outer diameter of the scaffold is being reduced in size by the crimp head, the crimping including:
increasing a retention between the scaffold and the balloon by raising the temperature of the scaffold to an elevated temperature of between Tg-low and 5 degrees centigrade above Tg-low, and
holding the crimp head at the crimped diameter for a dwell period while the scaffold has the elevated temperature;
wherein the scaffold is placed on the balloon such that when inflated a scaffold deployed diameter is at least 2.5 times higher than a crimped scaffold diameter.

2. The method of claim 1, further including the step of reducing elastic recoil in the crimped scaffold including placing the scaffold within a sheath to maintain balloon material between scaffold struts, wherein a scaffold diameter in the sheath is between 34% and 37% of the scaffold diameter prior to crimping.

3. The method of claim 1, wherein the dwell period is greater than 10 seconds.

4. The method of claim 3, wherein the scaffold further includes rings formed by ring struts, wherein prior to crimping a pair of ring struts adjoined at a crown are each orientated at an angle of between 20 and 30 degrees with respect to an axis perpendicular to a longitudinal axis of the scaffold.

5. The method of claim 3, wherein the scaffold further includes rings formed by ring struts, wherein prior to crimping an angle of between 120 and 130 degrees spans between a pair of adjoined ring struts.

6. The method of claim 1, wherein the polymer is poly(L-lactide) (PLLA) and the temperature during crimping is 55+/−3° C.

7. A method of making a balloon-expanded scaffold, comprising:
using a scaffold made from a polymer characterized by a glass transition temperature (Tg) having a lower limit (Tg-low); and
crimping the scaffold to a balloon, including:
a first diameter reduction, followed by a first dwell period, and
a second diameter reduction, followed by a second dwell period,
wherein the period for the second dwell is at least 10 times longer than the period for the first dwell, and
wherein the scaffold temperature during crimping is between Tg-low and 5 degrees centigrade above Tg-low.

8. The method of claim 7, wherein the polymer is poly(L-lactide) (PLLA) and the temperature during crimping is 55+/−3° C.

9. The method of claim 7, wherein the crimping is performed within a crimp head, the crimping further comprising moving the crimp head to a diameter that is at least 2.5 times smaller than a diameter of the scaffold prior to crimping.

10. The method of claim 7, further including the step of deionizing the scaffold before crimping.

11. The method of claim 7, wherein the crimping is performed within a crimp head having a crimping blade, and a sheet of material is disposed between the blade and the scaffold during crimping.

12. The method of claim 7, wherein the crimping is performed within a crimp head, the crimping further comprising moving the crimp head to a diameter that is at least 2.5 to 3.0 times smaller than a scaffold deployed diameter.

13. The method of claim 7, wherein the crimping temperature is between 50° C. and 55° C.

14. The method of claim 13, wherein the polymer comprises poly(lactide-co-glycolide) (PLGA).

15. The method of claim 7, further including the step of reducing elastic recoil in the crimped scaffold including placing the scaffold within a sheath to maintain balloon material between scaffold struts, wherein a scaffold diameter in the sheath is between 34% and 37% of the scaffold diameter prior to crimping.

16. A method of making a balloon-expandable scaffold, comprising:
using a scaffold having struts made from a polymer characterized by a glass transition temperature (Tg),
crimping the scaffold to a balloon, including:
heating the scaffold to a crimping temperature,
inflating the balloon,
reducing a scaffold diameter to a first diameter while the balloon is inflated, and
reducing the scaffold diameter to a second diameter that is smaller than the first diameter, wherein the reducing to the first diameter occurs at a slower rate than the reducing to the second diameter.

17. The method of claim 16, wherein prior to crimping a pair of the struts adjoined at a crown are each orientated at an angle of between 20 and 30 degrees with respect to an axis perpendicular to a longitudinal axis of the scaffold.

18. The method of claim 16, further including the step of reducing elastic recoil in the crimped scaffold including placing the scaffold within a sheath to maintain material of the balloon between struts of the scaffold, wherein a scaffold diameter in the sheath is between 34% and 37% of a scaffold diameter prior to crimping.

19. The method of claim 16, wherein the balloon is inflated during both the reducing a scaffold diameter to a first diameter and the reducing a scaffold diameter to a second diameter step.

20. The method of claim 19, wherein a balloon pressure is less during the reducing a scaffold diameter to a second diameter step than the balloon pressure during the reducing a scaffold diameter to a first diameter step.

21. The method of claim 16, wherein the crimping is performed within a crimp head, the crimping further comprising moving the crimp head to a diameter that is at least 2.5 times smaller than a diameter of the scaffold prior to crimping.

* * * * *